(12) United States Patent
Li et al.

(10) Patent No.: US 10,682,332 B2
(45) Date of Patent: Jun. 16, 2020

(54) METHOD FOR TREATING MELANOMA

(71) Applicant: Huanggang normal University, Huanggang (CN)

(72) Inventors: Shiming Li, Glastonbury, CT (US); Tao Long, Huanggang (CN); Guliang Yang, Huanggang (CN); Xiaojian Lv, Huanggang (CN); Yin Xu, Huanggang (CN); Ting Zhang, Huanggang (CN)

(73) Assignee: Huanggang Normal University, Huanggang, Hubei (CN)

( * ) Notice: Subject to any disclaimer, the term of this patent is extended or adjusted under 35 U.S.C. 154(b) by 215 days.

(21) Appl. No.: 15/675,699

(22) Filed: Aug. 11, 2017

(65) Prior Publication Data
US 2019/0046498 A1 Feb. 14, 2019

(51) Int. Cl.
*A61K 31/352* (2006.01)
*A61K 8/97* (2017.01)
*A61K 31/00* (2006.01)
*A61Q 19/00* (2006.01)

(52) U.S. Cl.
CPC .............. *A61K 31/352* (2013.01); *A61K 8/97* (2013.01); *A61K 31/00* (2013.01); *A61Q 19/00* (2013.01)

(58) Field of Classification Search
None
See application file for complete search history.

(56) References Cited

FOREIGN PATENT DOCUMENTS

CN       107007591 A    *   8/2017

* cited by examiner

*Primary Examiner* — Terry A McKelvey
*Assistant Examiner* — Catheryne Chen
(74) *Attorney, Agent, or Firm* — Bin Lu

(57) ABSTRACT

Disclosed is a method of inhibiting growth of a melanoma cancer cell. The method includes contacting the melanoma cancer cell with an effective amount of a composition and the composition contains polymethoxyflavone. The polymethoxyflavone can be applied in an amount of 0.1 μmol/L-1000 μmol/L. A method of treating a subject having melanoma with the above discussed composition is also included.

15 Claims, 3 Drawing Sheets

2% DMSO control group 5-hydroxy-3,6,7,8,3',4'-hexamethoxyflavone treatment group

METHOD FOR TREATING MELANOMA

FIELD OF THE INVENTION

The present invention relates generally to the field of cancer therapeutics. Particularly, it relates to use of a therapeutic agent to treat melanoma in human or animal subjects. More specifically, the present invention provides polymethoxyflavones as a therapeutic agent(s).

BACKGROUND OF THE INVENTION

Melanoma, a cancer usually grown out of melanocytes in the skin, mucous membranes, or luminal membrane, is the most malignant form of skin cancer. It is prone to metastasis when melanoma cells spread to distant sites in the body. Statistics indicates that more than 80% of skin cancer deaths are due to melanoma. Melanoma can develop anywhere on the skin, including the skin at body truck, feet, toes, or fingers.

It is likely that a number of factors, e.g., environmental and genetic ones, contribute to the development of melanoma. For Caucasians in many developed countries, exposure to ultraviolet (UV) radiation from the sun is believed to be the main cause for melanoma when the UV radiation brings about DNA mutations in the skin cells. However, the etiology for melanoma in Asian or African, particularly the so-called acral melanoma, is not well understood.

Treatment of melanoma remains a great challenge today as the 5-year survival rates, which are highly correlated to the development stage of the cancer when initially detected, are 94%, 44%, 38%, and 4.6% for patients with stage I, stage II, stage III, and stage IV melanoma, respectively. Patients with early stage melanoma, after confirmed by biopsy, are generally treated with surgery on primary tumors, whereas those with late stage tumors, often require radiotherapy or chemotherapy after the surgical resection. Clearly, to find a therapy to improve survival rates for melanoma patients is imperative as the current survival number, especially for those with late stage tumors, is very low.

Because patients with late stage melanoma depend heavily on radiotherapy or chemotherapy, there remains an urgent need to develop effective therapeutic agents for treating and/or prevention of melanoma.

SUMMARY OF THE INVENTION

The present invention provides a method of using phytochemicals as therapeutic agents to treat melanoma. This naturally derived agent exhibits through studies an unexpectedly strong inhibitory activity on melanoma cancer cells, thus providing a safe and effective way to treat an otherwise difficult disease.

One aspect of this invention relates to a method of inhibiting growth of a melanoma cancer cell, the method includes contacting the melanoma cancer cell with an effective amount of a composition and the composition contains polymethoxyflavones.

Examples of the polymethoxyflavone described above include hesperetin, hesperidin, nobiletin, tangeretin, sinensetin, 3,5,6,7,3',4'-hexamethoxyflavone, 3,5,6,7,8,3',4'-heptamethoxyflavone, 3,5,7,3',4'-pentamethoxyflavone, 5,6,7,4'-tetramethoxyflavone, 5-hydroxy-6,7,8,3',4'-pentamethoxyflavone, 5-hydroxy-6,7,8,4'-tetramethoxyflavone, 5-hydroxy-6,7,3',4'-tetramethoxyflavone, gardenin, 5-hydroxy-3,6,7,8,3',4'-hexamethoxyflavone, 5-hydroxy-3,6,7,3',4'-pentamethoxyflavone, 5-hydroxy-6,7,4'-trimethoxyflavone, or a combination thereof.

Preferably, the composition contains 5-hydroxy-3,6,7,8,3',4'-hexamethoxyflavone.

The polymethoxyflavone can be applied in an amount of 0.1 μmol/L-1000 μmol/L.

Another aspect of this invention relates to a method of inhibiting tumorigenesis of a melanoma cancer cell. The method includes treating the melanoma cancer cell with an effective amount of a composition and the composition contains polymethoxyflavones.

Examples of the polymethoxyflavone are enumerated above and the polymethoxyflavone can be applied also in an amount of 0.1 μmol/L-1000 μmol/L. Advantageously, the composition contains 5-hydroxy-3,6,7,8,3',4'-hexamethoxyflavone.

Examples of the melanoma cancer cells discussed above include human melanoma cancer cell A2058 and cell A375. Prior to the step of treating the melanoma cancer cell, the method can further include transplanting the melanoma cancer cell in a laboratory animal. The transplanted human melanoma cancer cell can be an A375 cell and the laboratory animal can be a C57BL/6 mouse.

Yet another aspect of this invention relates to a method of treating a subject having melanoma. The method includes administering to the subject with a therapeutically effective amount of a composition and the composition contains polymethoxyflavones.

Again, examples of the polymethoxyflavones are enumerated above and the polymethoxyflavone can be administered in an amount of 0.1 μmol/L-1000 μmol/L. A preferred example of the polymethoxyflavone is 5-hydroxy-3,6,7,8,3',4'-hexamethoxyflavone.

The details of the invention are set forth in the drawing and description below. Other features, objects, and advantages of the invention will be apparent from the description and from the claims.

BRIEF DESCRIPTION OF THE DRAWINGS

These drawings illustrate certain aspects of some of the embodiments of the present invention, and should not be used to limit or define the invention.

DETAILED DESCRIPTION

Figure 1:
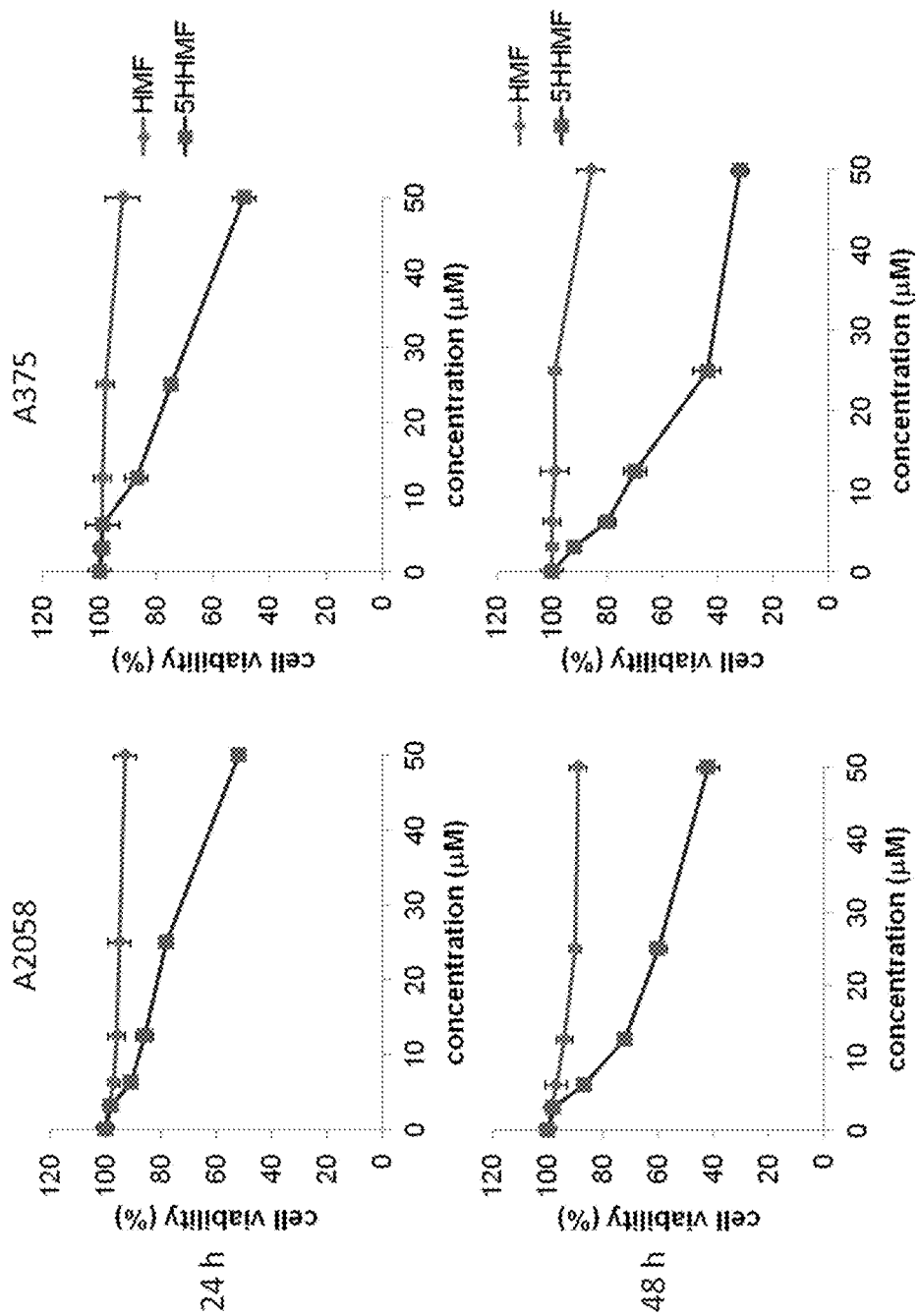
FIG. 1 is a diagram illustrating growth inhibition by 5-hydroxy-3,6,7,8,3',4'-hexamethoxyflavone (5HHMF) in human melanoma cancer cells A2058 and A375.

Polymethoxyflavones are a class of flavonoids with 2 or more methoxy groups, which are widely found in plants, especially in the genus *Rutaceae*. Polymethoxyflavones can be purified by supercritical repeated silica gel column chromatography, $CO_2$ supercritical extraction, ultrasonic-assisted ion exchange, high-speed countercurrent chromatography, or other extract/separation methods. Extracted polymethoxyflavones have been studied for a wide range of potential medicinal purposes, e.g., inhibition of growth of cancer cells, anti-inflammatory activity, anti-oxidative activity, prevention of cardiovascular or cerebrovascular diseases, inhibition of pathogen growth, and other medicinal applications.

The polymethoxyflavone used in the method of the present invention can be a flavone substituted by two or more of methoxyl and by one or more of hydroxyl. Examples include 5-hydroxy-3,6,7,8,3',4'-hexamethoxyflavone, 5-hydroxy-3,6,7,3',4'-pentamethoxyflavone, 5-hydroxy-6,7,4'-trimethoxyflavone, and an analog thereof.

5-hydroxy-3,6,7,8,3',4'-hexamethoxyflavone (IUPAC name: 5-hydroxy-3,6,7,8,3',4'-hexamethoxyflavone or 2-(3,4-dimethoxy-phenyl)-5-hydroxy-3,6,7,8-tetramethoxy-chromen-4-one, CAS number: 1176-88-1) can be prepared as described above. The 5-hydroxy-3,6,7,8,3',4'-hexamethoxyflavone solution used herein was prepared by dissolving in 2% DMSO.

Many melanoma cancer patients were diagnosed at the late stage of the disease, facing a dismally low survival rate. These patients often require either radiotherapy or chemotherapy. However, the outcome of the treatments remains unsatisfactorily poor. The method described in the present invention provides a therapy to treat melanoma cancer by using polymethoxyflavone. This therapy has been shown by studies in cell lines and animal models to be more effective in treating cancer. Because of the phytochemical nature of the agent used in this therapy, it would likely cause fewer side effects of chemotherapy, and lower the overall treatment costs.

The term "a subject having melanoma" used herein generally refers to a patient having melanoma or any patient having melanoma. The term "a patient" includes a treatment-naive patient as well as a treatment-experienced patient. The term "melanoma" includes melanoma of any stages. All patients having melanoma are preferably treated by wide excision of the primary melanoma lesion prior to initiation of the therapy provided by the present invention.

The method of the present invention has been shown to inhibit the growth of human melanoma cancer cells. The study was conducted using human melanoma cancer cell line A2058 or A375 as follows: culturing the cell line in DMEM medium; adding 5-hydroxy-3,6,7,8,3',4'-hexamethoxyflavone with varying concentrations (3.125, 6.25, 12.5, 25, 50 μmol in 100 μl of 2% DMSO solution per liter of the medium); collecting the control and treated cells after 48 hrs of culturing and determining the cell viability by measuring light absorbance of the cells; and calculating the $IC_{50}$ rate in the human melanoma cancer cells.

Further, the instant method has been shown to inhibit the tumor growth in melanoma cancer cell-engrafted C57BL/6 nude mice. The study was carried out as follows: inoculating C57BL/6 mice with of the human melanoma cancer cells; dividing the mice into 2 groups with 8 mice in each group and treating them once every two days with (i) 0.4 ml of 2% DMSO, (ii) 0.4 ml of 2% DMSO containing 0.5 μmol of 5-hydroxy-3,6,7,8,3',4'-hexamethoxyflavone; measuring tumor sizes after animal sacrificing 28 days post tumor cell inoculation.

Results obtained from the study exhibited that the therapy of the present invention had a strong activity in inhibiting the growth of human melanoma cancer cell as well as the growth of tumor derived from the melanoma cancer cell engrafted in mice.

EXAMPLES

Example 1: Effects of Combining 5-hydroxy-3,6,7,8,3',4'-hexamethoxyflavone on the Growth and Cell Cycle Distribution of Human Melanoma Cancer Cell A2058 and Cell A375

Growth Inhibition

The cells derived from human melanoma lines A2058 and A375 were cultured in DMEM medium containing 100 U/mL penicillin, 100 μg/ml streptomycin, and 10% fetal bovine serum at a temperature of 37° C. and with carbon dioxide at a concentration of 5%. The cultured cells were divided into 6 study groups and each would be treated with 5-hydroxy-3,6,7,8,3',4'-hexamethoxyflavone of a different concentration. The preparation was as follows: first, 3.125, 6.25, 12.5, 25, and 50 μmol 5-hydroxy-3,6,7,8,3',4'-hexamethoxyflavone solutions were prepared with 2% DMSO; then for every liter of the culturing media, 100 μL of 3.125, 6.25, 12.5, 25, and 50 μmol 5-hydroxy-3,6,7,8,3',4'-hexamethoxyflavone prepared solutions were added to study groups 2, 3, 4, 5, and 6, respectively. 2% DMSO control solution was added to study group 1. After culturing for 48 hrs, the cells were collected and the absorbance of each treatment group was measured for calculating the $IC_{50}$ rate in human melanoma cancer cell A2058 by the treatment. A parallel study for human melanoma cancer cell A375 was conducted following the same protocol. The results are presented in FIG. 1 and show clearly that 5-hydroxy-3,6,7,8,3',4'-hexamethoxyflavone inhibited the growth of human melanoma cancer cell A2058 as well as cell A375.

Cell Cycle Arrest

To further elucidate the mechanism of growth inhibition of the human melanoma cancer cells by 5-hydroxy-3,6,7,8,3',4'-hexamethoxyflavone, another study was carried out using only human melanoma cancer cell A375 and 3 study groups. In one liter of the culturing media, 100 μL of 25 and 50 μmol of 5-hydroxy-3,6,7,8,3',4'-hexamethoxyflavone prepared solutions were added to two study groups. The control group was only treated with 2% DMSO solution.

The studied cells were incubated for 24 hrs before collected in a centrifuge tube. The cells were then washed with PBS at 4° C. and n mixed with 70% ethanol pre-cooled at −20° C. before kept at 4° C. overnight. Next, the cells were centrifuged at 1000 rpm to remove ethanol and the cell density was adjusted to (1-2)×10⁶ cells/mL by add PBS. Following adding PI and DNase-free RNase to respectively reach final concentrations of 50 μg/mL and 50 g/mL, the cells were stained for cell cycle and apoptosis studies by flow cytometry. All studies were repeated 3 times and the averages were calculated.

Figure 2:
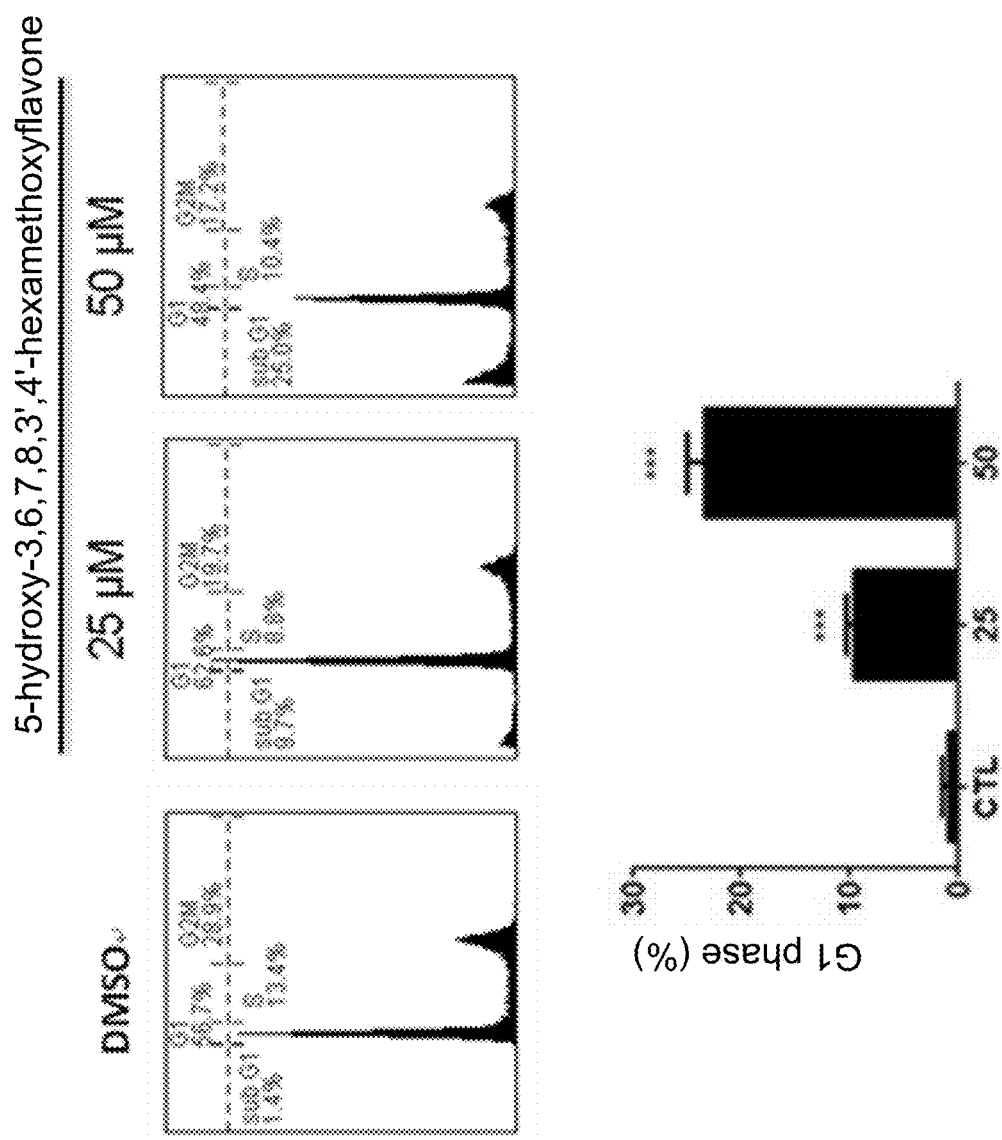
FIG. 2 is a diagram and bar plot that show effect of apoptosis by 5-hydroxy-3,6,7,8,3',4'-hexamethoxyflavone in human melanoma cancer cell A375.

The results presented in FIG. 2 show that 5-hydroxy-3,6,7,8,3',4'-hexamethoxyflavone promoted the G1 phase accumulation for the treated cancer cells. Specifically, G1 phase cells accounted for 9.4% and 25% of the total cells treated with 25 and 50 μmol drug solution, respectively. By contrast, G1 phase cells only accounted for only 1.4% in the control group. The results demonstrate that 5-hydroxy-3,6,7,8,3',4'-hexamethoxyflavone could induce much more cell cycle arrest in the melanoma cancer cells and lead to their apoptosis much more effectively.

Example 2: Effects of 5-Hydroxy-3,6,7,8,3',4'-Hexamethoxyflavone on Tumor Growth in Human Melanoma Cancer Cell-Engrafted C57BL/6 Mice The experimental C57BL/6 mice were divided into 2 groups, with 8 in each group. Each mouse was fed with 0.4 mL of 0.5 µmol 5-hydroxy-3,6,7,8,3',4'-hexamethoxyflavone solution as in the treatment group or with 0.4 mL 2% DMSO solution as in the control group at a frequency of once every 2 days. Each mouse was inoculated with human melanoma cancer cell A375 following a standard protocol. 28 days after of the inoculation, the mice were sacrificed. Finally, sizes of tumors in each group of mice were measured and their averages were calculated.

Figure 3:
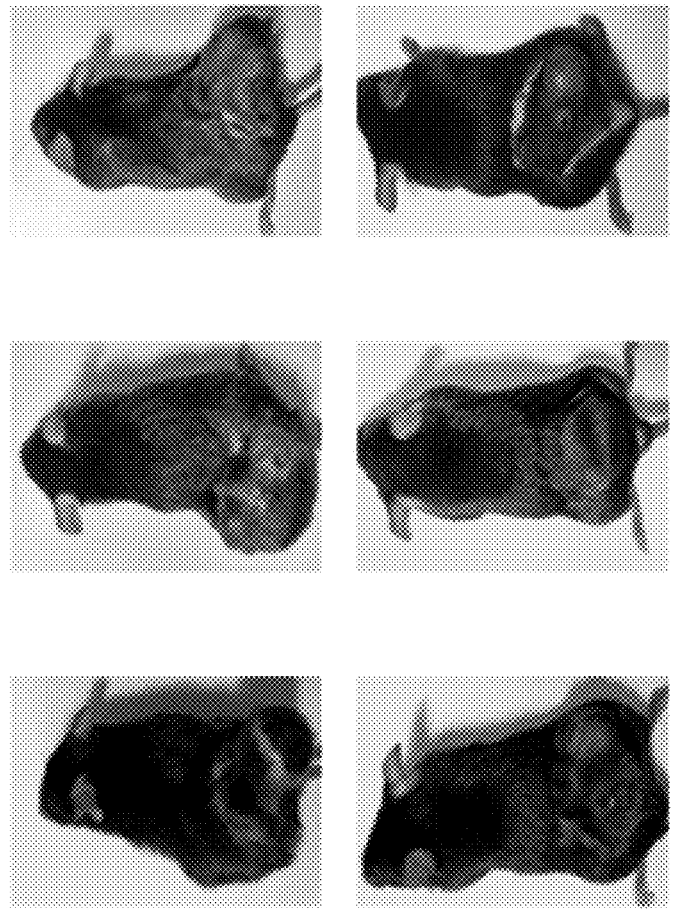
FIG. 3 is a diagram showing that 5-hydroxy-3,6,7,8,3',4'-hexamethoxyflavone inhibited tumor growth in C57BL/6 mice engrafted with melanoma cancer cell A375.

The results presented in FIG. 3 show that while the average tumor in the control group had a size of 2450 mm$^3$, that in 5-hydroxy-3,6,7,8,3',4'-hexamethoxyflavone treated group had an unexpectedly low size, i.e., only 890 mm$^3$, indicating that the applied drug had a strong activity inhibiting the growth of tumors in human melanoma cancer cell A375-engrafted C57BL/6 mice.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Further, from the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of inhibiting growth of a melanoma cancer cell, the method comprising contacting the melanoma cancer cell with an effective amount of a composition, wherein the composition comprises polymethoxyflavones.

2. The method of claim 1, wherein the polymethoxyflavone is hesperetin, nobiletin, sinensetin, hesperidin, tangeretin, 3,5,6,7,3',4'-hexamethoxyflavone, 3,5,6,7,8,3',4'-heptamethoxyflavone, 3,5,7,3',4'-pentamethoxyflavone, 5,6,7,4'-tetramethoxyflavone, 5-hydroxy-6,7,8,3',4'-pentamethoxyflavone, 5-hydroxy-6,7,8,4'-tetramethoxyflavone, 5-hydroxy-6,7,3',4'-tetramethoxyflavone, gardenin, 5-hydroxy-3,6,7,8,3',4'-hexamethoxyflavone, 5-hydroxy-3,6,7,3',4'-pentamethoxyflavone, 5-hydroxy-6,7,4'-trimethoxyflavone, or a combination thereof.

3. The method of claim 2, wherein the polymethoxyflavone is 5-hydroxy-3,6,7,8,3',4'-hexamethoxyflavone.

4. The method of claim 1, wherein the polymethoxyflavone is applied in an amount of 0.1 µmol/L-1000 µmol/L.

5. The method of claim 1, wherein the melanoma cancer cell is human melanoma cancer cell A2058 or cell A375.

6. A method of inhibiting tumorigenesis of a melanoma cancer cell, the method comprising treating the melanoma cancer cell with an effective amount of a composition, wherein the composition comprises polymethoxyflavone.

7. The method of claim 6, wherein the polymethoxyflavone is hesperetin, nobiletin, sinensetin, hesperidin, tangeretin, 3,5,6,7,3',4'-hexamethoxyflavone, 3,5,6,7,8,3',4'-heptamethoxyflavone, 3,5,7,3',4'-pentamethoxyflavone, 5,6,7,4'-tetramethoxyflavone, 5-hydroxy-6,7,8,3',4'-pentamethoxyflavone, 5-hydroxy-6,7,8,4'-tetramethoxyflavone, 5-hydroxy-6,7,3',4'-tetramethoxyflavone, gardenin, 5-hydroxy-3,6,7,8,3',4'-hexamethoxyflavone, 5-hydroxy-3,6,7,3',4'-pentamethoxyflavone, 5-hydroxy-6,7,4'-trimethoxyflavone, or a combination thereof.

8. The method of claim 7, wherein the polymethoxyflavone is 5-hydroxy-3,6,7,8,3',4'-hexamethoxyflavone.

9. The method of claim 6, wherein the polymethoxyflavone is applied in an amount of 0.1 µmol/L-1000 µmol/L.

10. The method of claim 6, wherein the melanoma cancer cell is human melanoma cancer cell A2058 or cell A375.

11. The method of claim 6, further comprising, prior to the step of treating the melanoma cancer cell, transplanting the melanoma cancer cell in a laboratory animal, wherein the melanoma cancer cell is human melanoma cancer cell A375 and the laboratory animal is a C57BL/6 mouse.

12. A method of treating a subject having melanoma, the method comprising administering to the subject a therapeutically effective amount of a composition, wherein the composition comprises polymethoxyflavone.

13. The method of claim 12, wherein the polymethoxyflavone is hesperetin, nobiletin, sinensetin, hesperidin, tangeretin, 3,5,6,7,3',4'-hexamethoxyflavone, 3,5,6,7,8,3',4'-heptamethoxyflavone, 3,5,7,3',4'-pentamethoxyflavone, 5,6,7,4'-tetramethoxyflavone, 5-hydroxy-6,7,8,3',4'-pentamethoxyflavone, 5-hydroxy-6,7,8,4'-tetramethoxyflavone, 5-hydroxy-6,7,3',4'-tetramethoxyflavone, gardenin, 5-hydroxy-3,6,7,8,3',4'-hexamethoxyflavone, 5-hydroxy-3,6,7,3',4'-pentamethoxyflavone, 5-hydroxy-6,7,4'-trimethoxyflavone, or a combination thereof.

14. The method of claim 13, wherein the polymethoxyflavone is 5-hydroxy-3,6,7,8,3',4'-hexamethoxyflavone.

15. The method of claim 12, wherein the polymethoxyflavone is administered in an amount of 0.1 µmol/L-1000 µmol/L.

* * * * *